US006839400B2

(12) United States Patent
Bruder et al.

(10) Patent No.: US 6,839,400 B2
(45) Date of Patent: Jan. 4, 2005

(54) IMAGE RECONSTRUCTION METHOD FOR COMPUTED TOMOGRAPHY

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 202 days.

(21) Appl. No.: 10/310,927

(22) Filed: Dec. 6, 2002

(65) Prior Publication Data

US 2003/0133533 A1 Jul. 17, 2003

(30) Foreign Application Priority Data

Dec. 6, 2001 (DE) .......................................... 101 59 927

(51) Int. Cl.$^7$ ................................................. H05G 1/60
(52) U.S. Cl. ............................. 378/4; 378/901; 378/15
(58) Field of Search ........................... 378/4, 8, 15, 19, 378/901

(56) References Cited

U.S. PATENT DOCUMENTS

| | | | | |
|---|---|---|---|---|
| 6,028,908 A | * | 2/2000 | Taguchi ........................ | 378/15 |
| 6,285,733 B1 | | 9/2001 | Proksa et al. ................. | 378/15 |

FOREIGN PATENT DOCUMENTS

| EP | 0990892 A2 | 4/2000 |
|---|---|---|
| WO | 9830980 | 7/1998 |

OTHER PUBLICATIONS

S.Z. Lee et al.; "True Three–Dimensional Come–Beam Reconstruction (TTCR) Algorithm"; IEEE, © 1989 vol. 8, pp. 304–312.

Stefan Schaller et al.; "Spiral Interpolation Algorithm for Multislice Spiral CT–Part I: Theory"; IEEE © ; vol. 19, No. 9; pp. 822–834.

* cited by examiner

*Primary Examiner*—David V. Bruce
*Assistant Examiner*—Elizabeth Keaney
(74) *Attorney, Agent, or Firm*—Harness, Dickey & Pierce, P.L.C.

(57) ABSTRACT

A method for computed tomography, includes, in order to scan an object to be examined with a conical beam originating from a focus and with a matrix-like detector array for detecting the beam, the focus is moved, relative to the object to be examined, on a focal path around a system axis. A detector array supplies an output data corresponding to received radiation. The output data is filtered, and the filtered output data is backprojected three-dimensionally in order to produce at least one slice of a layer of the, which has a layer thickness. The slice represents absorption values obtained from the output data of a voxel belonging to the layer for the radiation from the beam. Filtering is carried out at least also in the direction of the tangent to the focal path belonging to a respective focal position, and normalization is carried out for each voxel considered.

17 Claims, 3 Drawing Sheets

IMAGE RECONSTRUCTION METHOD FOR COMPUTED TOMOGRAPHY

The present application hereby claims priority under 35 U.S.C. §119 on German patent application number 10159927.7 filed Dec. 6, 2001, the entire contents of which are hereby incorporated herein by reference.

FIELD OF THE INVENTION

The present invention generally relates to an image reconstruction method for computed tomography.

BACKGROUND OF THE INVENTION

Current computed tomography systems scan an object to be examined with a conical beam originating from a focus and with a matrix-like detector array. A detector array supplies output data corresponding to a received radiation in the form of rays having a particular ray geometry.

The output data is filtered and then back-projected three-dimensionally in order to produce at least one slice of a layer of an object for examination.

Computed tomography methods of the indicated type are known under the term "filtered backprojection." However, as 3D methods, that is to say in conjunction with a matrix-like detector array, known methods do not provide an image quality which is judged to be adequate in practice. This is because "cone beam artifacts" occur due to the use of the conical X-ray beam.

Additionally disadvantageous in these methods is that redundant data are not used, such as data produced during spiral scanning with a small table advance as a result of multiple irradiation of one and the same voxel, which results in the incomplete use of an imaging radiation dose administered to the object.

Furthermore, there are considerations in connection with 2D methods for image reconstruction to proceed in such a way that preliminary images in large numbers are calculated from output data by "filtered backprojection", originating from sections of the focal path which are intrinsically inadequate for image reconstruction, the preliminary images being reformatted to form a final slice only in a second step. These 2D methods are less useful for detector arrays with a large width. That is, in the direction of the system axis, since then an extremely large number of preliminary images have to be processed, which is a problem even when there is a large amount of computing power available.

SUMMARY OF THE INVENTION

An embodiment of the present invention is based on an object of specifying a method for permitting an image quality to be enhanced.

According to an embodiment of the present invention, a method includes, in order to scan an object to be examined with a conical beam originating from a focus and with a matrix-like detector array for detecting the beam, the focus is moved, relative to the object to be examined, on a focal path around a system axis. The detector array supplies the output data corresponding to the received radiation in the form of rays with a fan ray geometry. Moreover, the output data is filtered, and the filtered output data is then back-projected three-dimensionally in order to produce at least one slice of a layer of the object to be examined which has a layer thickness. The slice represents absorption values obtained from the output data of the voxel belonging to the layer of the object to be examined for the radiation from the beam. The filtering is carried out at least also in the direction of the tangent to the focal path belonging to the respective focal position, and normalization is carried out for each voxel considered.

Accordingly, the filtering is carried out in the direction of the tangent to the focal path belonging to the respective focal position. Furthermore, the normalization is carried out in a voxel-specific manner, in particular for each voxel considered. It has been shown that, by way of the combination of this filtering according to the invention and the voxel-specific normalization, a particularly high image quality can be achieved. It is particularly advantageous if filtering is carried out in the aforementioned filter direction. The filter direction in this case corresponds to the direction of the projection of the spiral tangent onto the detector, the projection direction of course being determined by the connecting line from the focus to the center of rotation of the gantry.

The selection of this filter direction is based on the finding that the 2D method, which permits a high image quality and is based on preliminary images, would change into a 3D method if the sections of the focal path on which the calculation of preliminary images is based were to be shortened to such a great extent that it would still only cover a single projection, of which the data would then be filtered in the direction of the tangent to the focal path. Therefore, it would then be possible to expect such a 3D method would then permit a comparably good image quality to that of the 2D method.

Furthermore, as a result of the normalization for each voxel considered, care is taken at the same time that voxel-specific image artifacts, which could be produced by possible multiple strikes of rays of a voxel, are avoided.

A method according to an embodiment of the present invention may be implemented particularly easily when, before the filtering, the output data obtained in fan ray geometry in the form of rays $P(\alpha,\beta,q)$ is converted into parallel data present in parallel ray geometry in the form of rays $P(\theta,\beta,q)$ (azimuthal "rebinning") and $P(\theta,p,q)$ (complete "rebinning", that is to say azimuthal and radial "rebinning"). Therefore, with reference to FIG. 3

$\alpha$ is the focus angle
$\beta$ is the fan angle
q is the line index of the detector system corresponding to the z coordinate,
$\theta = \alpha + \beta$ is the parallel fan angle
$p = R_F \sin(\beta)$ is the parallel coordinate corresponding to the distance of the ray from the axis of rotation (system axis), and
$R_F$ is the radius of the focal path.

According to an embodiment of the present invention, the backprojection of the parallel data is carried out in such a way that, in the course of the backprojection for each voxel $(x,y,z)$ for each $\theta \in [0, \pi]$ for the rays $P(\theta+k\pi, {}^\beta, q)$ and $P(\theta+k\pi, {}^p, q)$, whose projection along the system axis goes through $(x,y)$, the sum $$P_{x,y,z}(\theta) = \sum_k \sum_q h\left(d_{x,y,z}\left(\theta+k\pi, \left\{\frac{\tilde{p}}{\tilde{\beta}}\right\}, q\right)\right) P\left(\theta+k\pi, \left\{\frac{\tilde{p}}{\tilde{\beta}}\right\}, q\right)$$

is formed, where x,y,z are the coordinates of the respective voxel,
k is a whole number corresponding to the number of half-revolutions of the focus included in the reconstruction, $\tilde{p}$ is the parallel coordinates of those rays whose projections along the system axis run through the coordinates (x,y) of a respective voxel (x,y,z), $\tilde{\beta}$ are the fan angles of those rays whose projections along the system axis run through the coordinates (x,y) of a respective voxel (x,y,z), and h is a weighting function that determines the layer thickness of the layer of the object to be examined displayed in the slice generated, and d is a function which is equal to the distance of the respective ray from the corresponding voxel (x,y) or depends on the distance of the respective ray from the corresponding voxel (x,y).

The expression $$\left\{ \begin{matrix} \tilde{p} \\ \tilde{\beta} \end{matrix} \right\}$$

in this(case expresses that the summing can be carried out optionally for rays obtained by way of azimuthal "rebinning" or by way of complete "rebinning", the filtering tangential to the focal path being a filtering in the β direction in the case of azimuthal "rebinning", and being a filtering in the p direction in the case of complete "rebinning".

As a result of summing both over k and q, it is then ensured that all the rays running through one and the same voxel are taken into account, and the radiation dose supplied to the object to be examined is therefore used completely. Another embodiment of the present invention provides that, in order to back-project the parallel data, the sum normalized as a sum H of the weights h $$H = \sum_k \sum_q h\left(d_{x,y,z}\left(\theta + k\pi, \left\{ \begin{matrix} \tilde{p} \\ \tilde{\beta} \end{matrix} \right\}, q\right)\right)$$

$$P_{x,y,z}(\theta) = \frac{1}{H} \sum_k \sum_q h\left(d_{x,y,z}\left(\theta + k\pi, \left\{ \begin{matrix} \tilde{p} \\ \tilde{\beta} \end{matrix} \right\}, q\right)\right) P\left(\theta + k\pi, \left\{ \begin{matrix} \tilde{p} \\ \tilde{\beta} \end{matrix} \right\}, q\right)$$

is formed. This procedure permits an image quality which is improved again, since possible overemphasis of voxels which are struck by more rays than other voxels is eliminated, and therefore corresponding artifacts are avoided. The CT value of the respective voxel is obtained by way of summation over θ.

The method according to an embodiment of the present invention may be used, for example, when according to one variant of the invention, the focal path is a circular path (tomogram scanning). According to a preferred variant of the present invention, the focal path is a spiral path, which is brought about by the focus being moved on a circular path about the system axis and, at the same time, there being a relative movement, between focus and object to be examined, in the direction of the system axis. On the basis of such spiral scanning, even relatively large volumes of the object to be examined can be examined without difficulty.

In the case of tomogram scanning, k is normally k=1 or k=2. In the case of spiral scanning, k is selected by taking account of the relative displacement in the direction of the system axis carried out per full revolution, in such a way that the area to be depicted of the object to be examined is registered completely.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
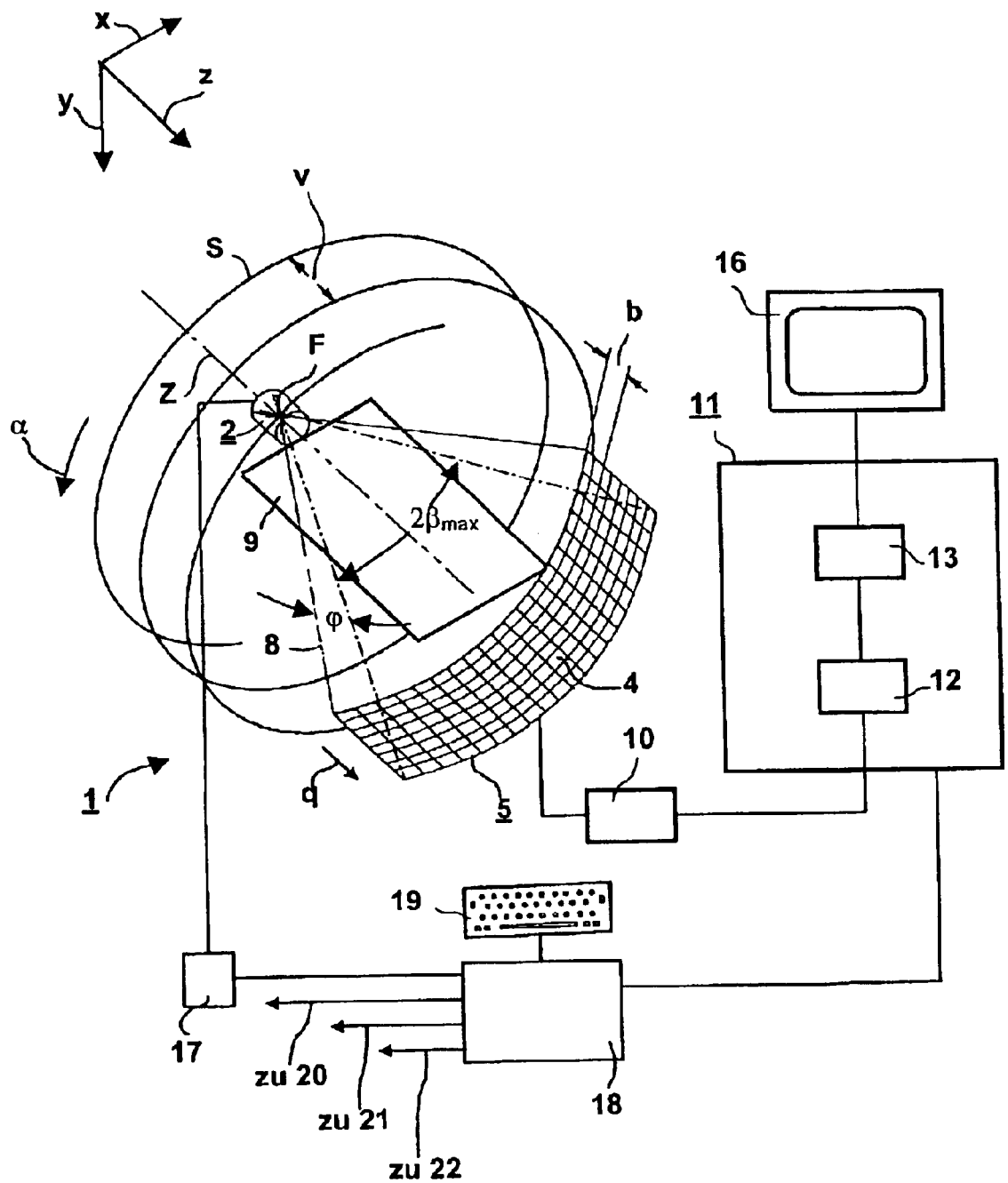
FIG. 1 illustrates a CT device having a plurality of lines of detector elements in an illustration which is partly perspective and partly in the form of a block diagram.
Figure 2:
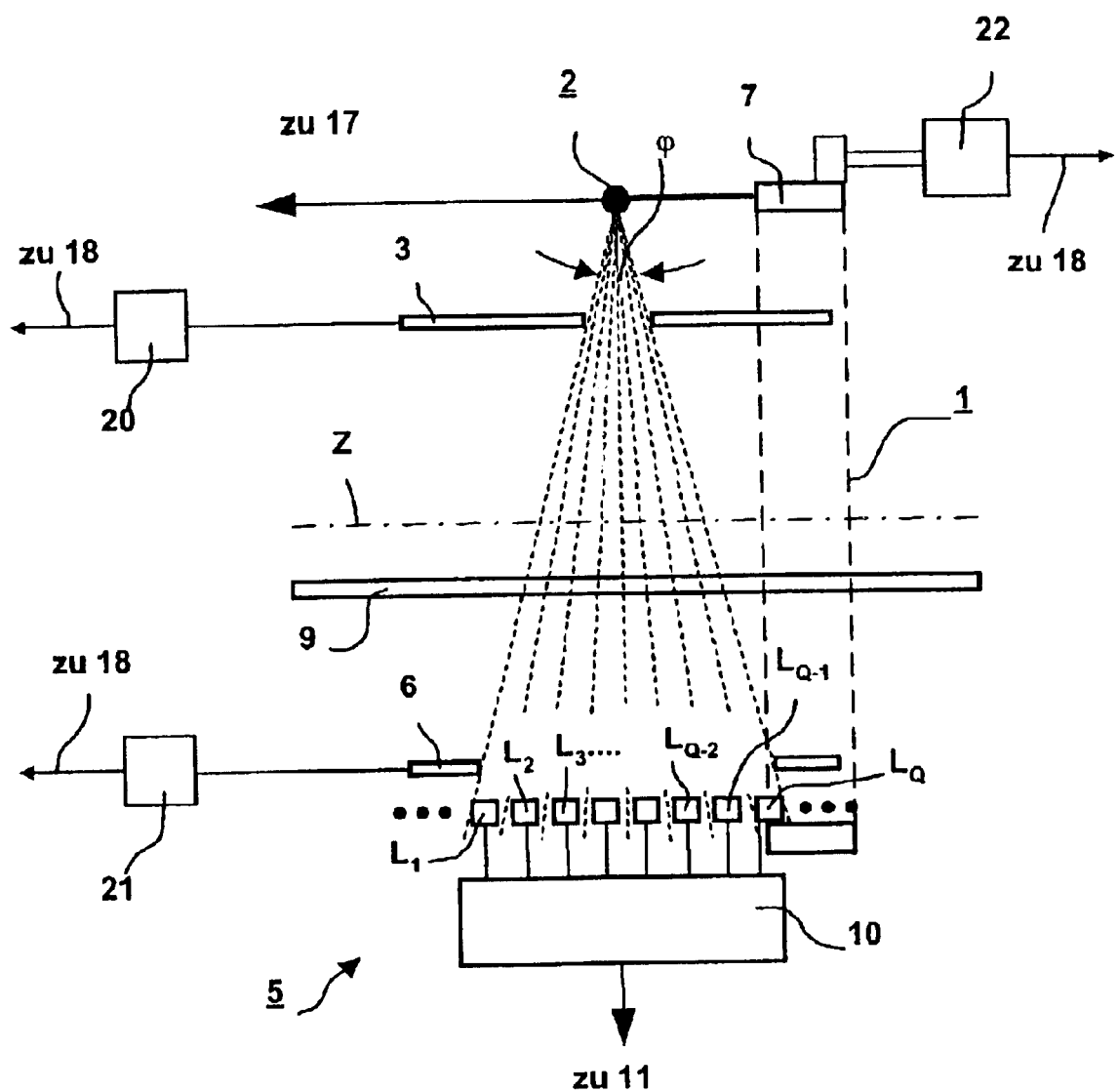
FIG. 2 illustrates a longitudinal section through the device according to FIG. 1.

FIGS. 1 and 2 illustrate a third generation computed tomography (CT) device, which is suitable for carrying out a method according to an embodiment of the present invention. A measuring arrangement of the CT device, designated overall by 1, has an X-ray source, designated overall by 2, with a radiation aperture 3 (FIG. 2) placed in front of it and close to the source, and a detector system 5 constructed as a two-dimensional array of a plurality of lines and columns of detector elements—one of these is designated by 4 in FIG. 1—with a radiation aperture 6 (FIG. 2) placed in front thereof and close to the detector. In FIG. 1, for reasons of clarity, only eight lines of detector elements 4 are illustrated, but the detector system 5 has further lines of detector elements 4, which is indicated by dots in FIG. 2.

As is illustrated in FIG. 2, the X-ray source 2 with the radiation aperture 3, on the one hand, and the detector system 5 with the radiation aperture 6, on the other hand, are fitted opposite each other on a rotary frame 7. Therefore, a pyramidal X-ray beam which, during the operation of the CT device, originates from the X-ray source 2 and is collimated by the adjustable radiation aperture 3 and whose edge rays are designated by 8, strikes the detector system 5. In the process, the radiation aperture 6 is set to correspond to the cross section of the X-ray beam set by way of the radiation aperture 3 in such a way that that area of the detector system 5 which can be struck directly by the X-ray beam is exposed. In the operating mode illustrated in FIGS. 1 and 2, this is eight lines of detector elements 4, which are referred to as active lines below. The further lines indicated by dots are covered by the radiation aperture 6 and therefore inactive.

Each line of detector elements 4 has a number K of detector elements, where βk=β1 to βK is the channel index, and each detector element is assigned a fan angle βk. The fan angle of the central detector element is equal to zero; the fan angles of the two outermost detector elements are β1=+βmax and βK=−βmax.

The active lines Lq of detector elements 4 are designated by L1 to LQ in FIG. 2, q=1 to Q being the line index which, in the case of an embodiment of the present invention described, corresponds to the z coordinate, so to speak.

The X-ray beam has the cone angle φ which is plotted in FIGS. 1 and 2, which is the opening angle of the X-ray beam in a plane containing the system axis Z and the focus F. The opening angle of the X-ray beam in a plane lying at right angles to the system axis Z and containing the focus F (fan opening angle) is 2βmax and is plotted in FIG. 1.

The rotary frame 7 can be set rotating about a system axis designated by Z by way of a drive device 22. The system axis Z runs parallel to the z axis of a three-dimensional rectangular coordinate system illustrated in FIG. 1.

The columns of the detector system 5 likewise run in the direction of the z axis, while the lines, whose width b is measured in the direction of the z axis and is 1 mm, for example, run transversely with respect to the system axis Z and the z axis.

In order to bring an object to be examined, for example a patient, into the beam path of the X-ray beam, a bearing device 9 is provided. The bearing device can be displaced parallel to the system axis Z, that is to say in the direction of the z axis, specifically in such a way that there is synchronization between the rotational movement of the rotary frame 7 and the translational movement of the bearing device. This has the effect that the ratio between translation and rotation speed is constant, this ratio being adjustable, by a desired value for the advance v of the bearing device being selected for each revolution of the rotary frame.

Therefore, it is possible for a volume of an object to be examined and located on the bearing device 9 to be examined in the course of volume scanning, it being possible for the volume scanning to be performed in the form of spiral scanning with the effect that, with simultaneous rotation of the measuring unit 1 and translation of the bearing device 9, a large number of projections from various projection directions is recorded by way of the measuring unit for each revolution of the measuring unit 1.

During the spiral scanning, the focus F of the X-ray source is moved relative to the bearing device 9 on a spiral path designated by S in FIG. 1. The spiral scanning must extend in the α direction over at least π+2βmax, in order to permit the complete reconstruction of a CT image for each line of detector elements, but it can also be longer as desired within the technical limits of the CT device.

However, because there are a plurality of lines of detector elements 4, a volume of the object to be examined can also be examined in the course of tomogram scanning, as it is known, in which there is no relative movement in the direction of the z axis between measuring unit 1 and bearing device 9 (v=0). In the case of tomogram scanning, therefore, the size of the volume examined is determined by the number of active lines of detector elements 4. During tomogram scanning, the focus F moves on a circular focal path which lies in a plane designated the mid-plane below.

The tomogram scanning can be carried out in the form of a partial revolution or in the form of a complete revolution, the partial revolution covering a partial revolution interval of at least π+2βmax (one half revolution plus fan opening angle), which permits complete reconstruction of a CT image, while a full revolution covers 2π.

The measured data read out in parallel from the detector elements of each active line of the detector system 5 during the spiral or tomogram scanning and corresponding to the individual projections P(α,β,q) in fan ray geometry is subjected to digital/analog conversion in a data conditioning unit 10, is serialized and transmitted to an image computer 11.

After the measured data has been preprocessed in a preprocessing unit 12 belonging to the image computer 11, the resultant data stream passes to a slice reconstruction unit 13. The slice reconstruction unit 13 uses the measured data to reconstruct slices of desired layers of the object to be examined in accordance with a method according to the present invention and still to be described in detail and based on "filtered backprojection".

The CT images are composed of pixels (pixel=picture element) assembled in the form of a matrix. The pixels are associated with the respective image plane, each pixel is assigned a CT number in Hounsfield units (HU) and the individual pixels are displayed in accordance with a CT-index/grey value scale with a grey value corresponding to their respective CT number. Accordingly, each pixel illustrates a voxel (voxel=volume element) of the layer of the object to be examined which is illustrated in the CT image. Since, because of the multi-line characteristic of the detector system 5 and, possibly, of the spiral scanning, measured data relating to a plurality of layers of the object to be examined is obtained, 3D data is available, which is subjected to 3D backprojection within the context of the present invention. As a result, 3D image data in the form of a three-dimensional matrix, for example with the axes x, y, z, is available, each element of the matrix corresponding to one voxel (x,y,z) and containing the grey value corresponding to the associated CT number. Those elements of the three-dimensional matrix which have the same x-, y- or z-value then constitute in each case a planar slice of the layer of the object to be examined which corresponds to the definitive x-, y- or z-value.

The images reconstructed by the slice reconstruction unit 13 are displayed on a display unit 16, for example a monitor, connected to the image computer 11.

The X-ray source 2, for example an X-ray tube, is supplied by a generator unit 17 with the requisite voltages and currents, for example the tube voltage U. In order to be able to set the latter to the respectively requisite value, the generator unit 17 is assigned a control unit 18 with keyboard 19, which permits the necessary settings.

In addition, the other operation and control of the CT device are carried out by way of the control unit 18 and the keyboard 19, which is illustrated by the fact that the control unit 18 is connected to the image computer 11.

Amongst other things, the number Q of the active lines of detector elements 4, and therefore the position of the radiation apertures 3 and 6, can be adjusted, for which purpose the control unit 18 is connected to the adjustment units 20 and 21 assigned to the radiation apertures 3 and 6. In addition, the rotation time τ can be adjusted, which is the time needed by the rotary frame 71 for a complete revolution and which is illustrated by the fact that the drive unit 22 associated with the rotary frame 7 is connected to the control unit 18.

Although it is in principle possible to implement a method according to an embodiment of the present invention in fan ray geometry as well, the CT device described is preferably operated in a mode in which a method according to an embodiment of the present invention is implemented in parallel beam geometry.

Accordingly, the data obtained during the scanning of the area of the body of the patient 8 which is relevant for the respective examination by way of spiral or tomogram scanning in fan ray geometry is first converted in a known manner into data in parallel ray geometry by a method generally designated "rebinning". This conversion is based on resorting the data obtained in fan ray geometry in such a way that the rays are removed from different projections recorded in fan ray geometry and are joined together to form a projection in parallel ray geometry.

In parallel ray geometry, data from an interval of length π is sufficient to be able to reconstruct a complete image. In order to obtain this data, nevertheless, data in fan ray geometry from an interval of length π+2βmax must be available.

Figure 3:
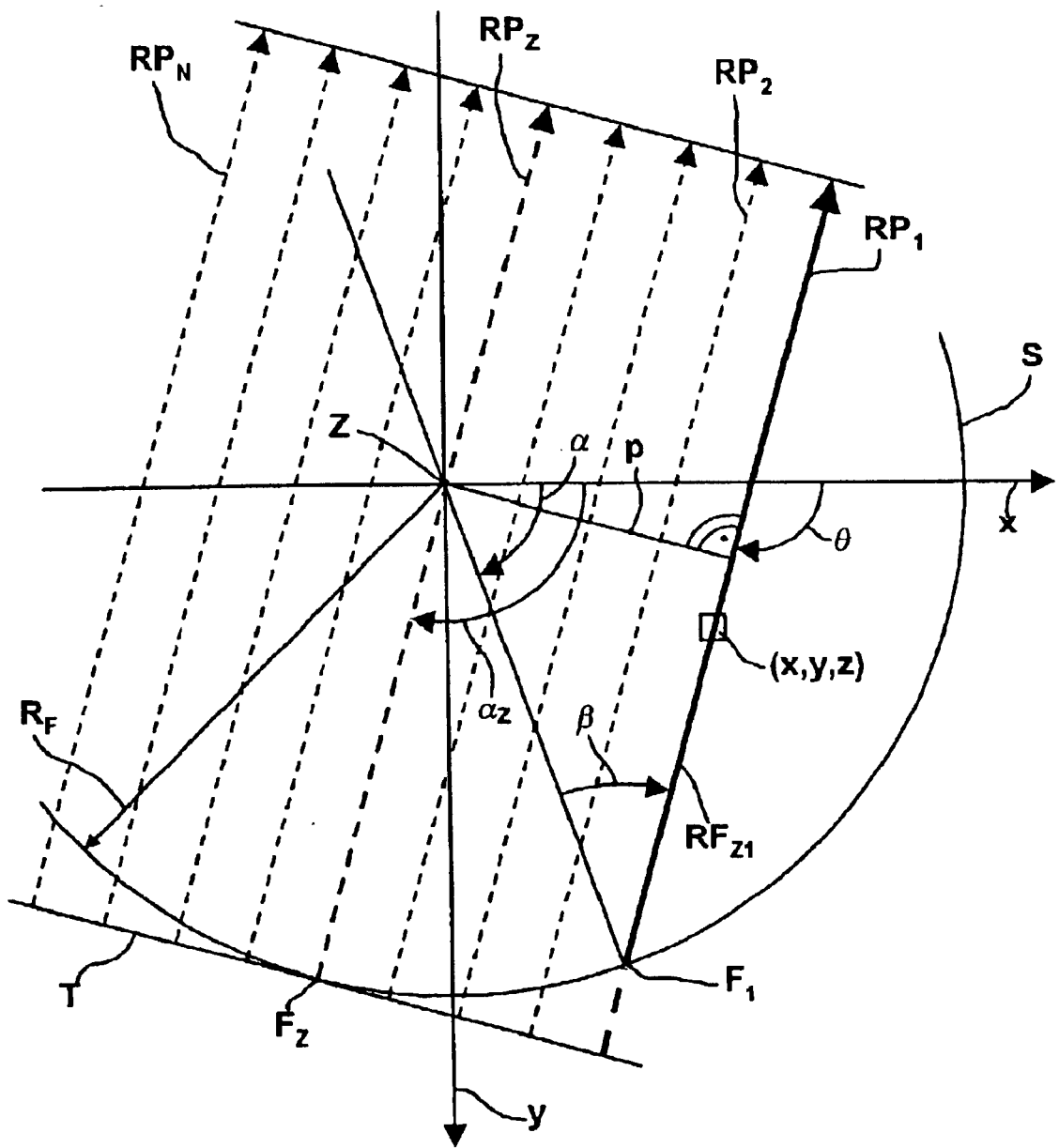
FIG. 3 is a diagram that illustrates "rebinning".

A projection in parallel ray geometry is illustrated in FIG. 3. According to this, all n parallel rays RP1 to RPN of this projection assume the parallel fan angle θ with respect to the x axis of the coordinate system illustrated in FIG. 3 and coinciding with that according to FIG. 1.

By using the parallel ray RP1 illustrated by a continuous line in FIG. 3, the change from fan ray to parallel ray geometry is to be explained below.

The parallel ray RP1 originates from a projection obtained for the focal position F1 lying on the focal path S in fan ray geometry. The central ray RFz1 belonging to this projection in fan ray geometry and running through the axis of rotation 6 and therefore the z axis of the coordinate system is likewise plotted in FIG. 3. The focal position F1 corresponds to the focus angle α1; this is the angle formed by the x axis and the central ray RFz1. As compared with the central ray RFz1, the ray RP1 has the fan angle β. It is therefore easy to see that the following is true for the parallel fan angle θ:

θ=α+β

The ray distance p from the axis of rotation 6 or the z axis, measured at right angles to the respective parallel ray, is given by p=R_F sin(β)

As is clear from the central ray RPZ illustrated by a thicker line in FIG. 3 and running through the axis of rotation 6 and the x axis, this ray is the central ray of a projection in fan ray geometry recorded in fan geometry for the focal position FZ at the focus angle αz. Since, for the central ray of a projection recorded in fan ray geometry it is true that β=0, it becomes clear that the following applies to the case of central rays:

Depending on whether an azimuthal or complete "rebinning" is carried out, the parallel projections are present in the form P(α,β,q)

or in the form

P(θ,p,q)

where

α is the focus angle
β is the fan angle
q is the line index of the detector system corresponding to the z coordinate,
θ=α+β is the parallel fan angle
p=R_F sin(β) is the parallel coordinate corresponding to the distance of the ray from the axis of rotation (system axis), and
R_F is the radius of the focal path.

In a first operating mode, which corresponds to a first embodiment of the method according to the present invention and can be selected by way of the keyboard 19, the above-described CT device operates on the basis of projections obtained by way of azimuthal "rebinning". The data corresponding to these projections is filtered in the β direction in the case of azimuthal "rebinnings", that is to say in each case in the direction of the tangent T belonging to the focal position of the central ray of the respective parallel projection (see FIG. 3), to be specific by using one of the filter cores which are usual in computed tomography, for example Shepp-Logon or Ramachandran-Lakshminarayanan core.

The parallel data filtered in this way are then backprojected in such a way that, in the course of the backprojection for each voxel (x,y,z) for each θ ∈[0, π] for the rays P(θ+kπ, $\tilde{β}$, q) and P(θ+kπ, $\tilde{p}$, q), whose projection along the system axis goes through (x,y), the sum $$P_{x,y,z}(\theta) = \sum_k \sum_q h(d_{x,y,z}(\theta + k\pi, \tilde{\beta}, q)) P(\theta + k\pi, \tilde{\beta}, q)$$

is formed, where x,y,z are the coordinates of the respective voxel,
k is a whole number corresponding to the number of half-revolutions of the focus included in the reconstruction,
$\tilde{p}$ is the parallel coordinates of those rays whose projections along the system axis run through the coordinates (x,y) of a respective voxel (x,y,z),
$\tilde{β}$ are the fan angles of those rays whose projections along the system axis run through the coordinates (x,y) of a respective voxel (x,y,z), and
h is a weighting function that determines the layer thickness of the layer of the object to be examined displayed in the slice generated, and d is a function which is equal to the distance of the respective ray from the corresponding voxel (x,y) or depends on the distance of the respective ray from the corresponding voxel (x,y).

Because of the selected filter direction and because of the summation both over k and over q, firstly cone beam artifacts are avoided and secondly, in the interests of high dose utilization, all the rays running through a voxel (x,y,z) are taken into account.

The absorption value μx,y,z associated with a voxel x,y,z is obtained by way of summation over θ over at least one half revolution, that is to say by forming $$\mu_{x,y,z} = \sum_\theta P_{x,y,z}(\theta)$$

The CT number corresponding to the respective absorption value is determined from the absorption value in a conventional way.

In this case, different weighting functions h and different functions d can be set by way of the keyboard 19.

A suitable weighting function h is, for example, a triangular or trapezoidal function.

The function d can be set the distance of the respective parallel ray from the voxel x,y,z or, instead, for example the z (axial) component of this distance.

In a modification of the first operating mode described above, for the backprojection of the parallel data, the sum normalized to the sum H of the weights h $$H = \sum_k \sum_q h(d_{x,y,z}(\theta + k\pi, \tilde{\beta}, q))$$

$$P_{x,y,z}(\theta) = \frac{1}{H}\sum_k \sum_q h(d_{x,y,z}(\theta + k\pi, \tilde{p}, q))P(\theta + k\pi, \tilde{p}, q)$$

is formed. This permits an image quality which is improved once more, since possible overemphasis of voxels which are "illuminated" in a plurality of half revolutions, that is to say are strike by rays, is eliminated and therefore corresponding artifacts are avoided. This redundancy occurs during spiral scanning when the relative displacement that takes place for each full revolution of the measuring arrangement is so low (low pitch) that voxels are irradiated repeatedly.

A second operating mode, which corresponds to a further embodiment of the method according to the present invention and can be selected by way of the keyboard 19, differs from the first operating mode in that the CT device described does not operate on the basis of projections obtained by way of azimuthal but by way of complete "rebinning". The data corresponding to these projections is filtered in the p direction in the case of complete "rebinning", that is to say in each case likewise in the direction of the tangent T belonging to the focal position of the central ray of the respective parallel projection (see FIG. 3).

Accordingly, for the parallel data filtered in this way in the course of the backprojection, the sum $$P_{x,y,z}(\theta) = \sum_k \sum_q h(d_{x,y,z}(\theta + k\pi, \tilde{p}, q))P(\theta + k\pi, \tilde{p}, q)$$

is formed, where $\tilde{p}$ are the parallel coordinates of those rays whose projections along the system axis run through the coordinates (x,y) of a respective voxel (x,y,z).

In the case of the second operating mode, too, in a modification of the backprojection of the parallel data, a sum normalized to the sum H of the weights h $$H = \sum_k \sum_q h(d_{x,y,z}(\theta + k\pi, \tilde{p}, q))$$

namely the sum $$P_{x,y,z}(\theta) = \frac{1}{H}\sum_k \sum_q h(d_{x,y,z}(\theta + k\pi, \tilde{p}, q))P(\theta + k\pi, \tilde{p}, q)$$

is formed.

In the case of the first and second operating modes described above, a functioning mode of a method according to the present invention is provided in which, in connection with a voxel (x,y,z), all those rays are considered whose projection along the axis of rotation 6 or the z axis goes through x, y. Whether and to what extent these rays are taken into account is determined by the weighting function h and the function d.

However, the CT device can also have further operating modes which can be selected by way of the keyboard 19 and which correspond to those previously described, with the difference that for a given focal position, the theoretical ray running through the respective voxel (x,y,z) is determined and then, taking account of the weighting function h and the function d, only those rays which can actually supply a contribution to the sum are included in the formation of the sum in the course of the backprojection.

In the case of the exemplary embodiments described, the relative movement between the measuring unit 1 and bearing device 9 is in each case produced by the bearing device 9 being displaced. However, within the scope of the present invention, there is also the possibility of leaving the bearing device 9 in a fixed position and instead of displacing the measuring unit 1. In addition, within the scope of the present invention, there is the possibility of producing the necessary relative movement by displacing both the measuring unit 1 and the bearing device 9.

The conical X-ray beam has a rectangular cross section in at least one exemplary embodiment described. However, other cross-sectional geometries are also possible within the scope of the invention.

In connection with the exemplary embodiments described above, CT devices of the third generation are used, that is to say the X-ray source and the detector system are displaced jointly about the system axis during the image generation. However, the present invention can also be used in conjunction with CT devices of the fourth generation, in which only the X-ray source is displaced about the system axis and interacts with a stationary detector ring, if the detector system is a multi-line array of detector elements.

A method according to an embodiment of the present invention can also be used in CT devices of the fifth generation, that is to say CT devices in which the X radiation does not originate from only one focus but from a plurality of foci of one or more X-ray sources displaced about the system axis, if the detector system has a multi-line array of detector elements.

The CT devices used in conjunction with the exemplary embodiments described above have a detector system with detector elements arranged in the manner of an orthogonal matrix. However, the present invention can also be used in conjunction with CT devices whose detector system has detector elements arranged in a two-dimensional array in another manner.

The exemplary embodiments described above relate to the medical application of the method according to the present invention. However, the present invention can also be applied outside medicine, for example in luggage checking or in material examination.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An image reconstruction method for computed tomography, comprising:

moving a focus on a focal path around a system axis relative to an object using a conical beam originating from the focus and a matrix-like detector array for detecting the beam;

supplying the detector array an output data corresponding to received radiation in the form of rays with a fan ray geometry;

filtering the output data; and backprojecting the filtered output data three-dimensionally to produce at least one slice of a layer of the object, the slice representing absorption values obtained from a voxel associated with the layer of the object, wherein the filtering is carried at least in a direction of a tangent to the focal path belonging to a respective focal position, and normalization is carried out for each voxel considered.

2. The method as claimed in claim 1, wherein before the filtering, the method includes converting output data in fan ray geometry in the form of rays $P(\alpha,\beta,q)$ into parallel data present in parallel ray geometry in the form of rays $P(\theta,\beta,q)$ and $P(\theta,p,q)$, where $\alpha$ is a focus angle $\beta$ is a fan angle q is a line index of the detector system corresponding to the z coordinate, $\theta = \alpha + \beta$ is a parallel fan angle $p = R_F \sin(\beta)$ is a parallel coordinate corresponding to the distance of the ray from the axis of rotation (system axis), and $R_F$ is the radius of a focal path.

3. The method as claimed in claim 2, further comprising forming, in the course of the backprojection for each voxel (x,y,z) for each $\theta \in [0, \pi]$ for the rays $P(\theta+k\pi, \beta, q)$ and $P(\theta+k\pi, \tilde{p}, q)$, whose projection along the system axis goes through (x,y), the sum $$P_{x,y,z}(\theta) = \sum_k \sum_q h\left(d_{x,y,z}\left(\theta+k\pi, \left\{\frac{\tilde{p}}{\tilde{\beta}}\right\}, q\right)\right) P\left(\theta+k\pi, \left\{\frac{\tilde{p}}{\tilde{\beta}}\right\}, q\right)$$

where x,y,z are coordinates of the respective voxel, k is a whole number corresponding to a number of half-revolutions of the focus included in a reconstruction, $\tilde{p}$ are parallel coordinates of those rays whose projections along the system axis run through coordinates (x,y) of a respective voxel (x,y,z), $\tilde{\beta}$ are fan angles of those rays whose projections along the system axis run through the coordinates (x,y) of a respective voxel (x,y,z), and h is a weighting function that determines the layer thickness of the layer of the object displayed in the slice generated, and d is a function which is equal to a distance of the respective ray from the corresponding voxel (x,y) or depends on the distance of a respective ray from the corresponding voxel (x,y).

4. The method as claimed in claim 3, further comprising normalizing and forming, during the backprojection of the parallel data, the sum to the sum H of the weights h, where $$H = \sum_k \sum_q h\left(d_{x,y,z}\left(\theta+k\pi,\left\{\frac{\tilde{p}}{\tilde{\beta}}\right\},q\right)\right)$$

$$P_{x,y,z}(\theta) = \frac{1}{H} \sum_k \sum_q h\left(d_{x,y,z}\left(\theta+k\pi,\left\{\frac{\tilde{p}}{\tilde{\beta}}\right\},q\right)\right) P\left(\theta+k\pi,\left\{\frac{\tilde{p}}{\tilde{\beta}}\right\},q\right).$$

5. The method as claimed claim 1, wherein the filtering is carried out in the direction of the tangent to the focal path belonging to the respective focal position.

6. The method as claimed in claim 1, wherein the focal path is a circular path.

7. The method as claimed in claim 1, wherein the focal path is a spiral path, the spiral path being generated as the focus is moved on a circular path about the system axis.

8. The method as claimed in claim 7, wherein the spiral path is further generated in accordance with a relative movement of the focus in a direction of the system axis.

9. The method as claimed claim 2, wherein the filtering is carried out in the direction of the tangent to the focal path belonging to the respective focal position.

10. The method as claimed claim 3, wherein the filtering is carried out in the direction of the tangent to the focal path belonging to the respective focal position.

11. The method as claimed claim 5, wherein the filtering is carried out in the direction of the tangent to the focal path belonging to the respective focal position.

12. The method as claimed in claim 2, wherein the focal path is a circular path.

13. The method as claimed in claim 3, wherein the focal path is a circular path.

14. The method as claimed in claim 4, wherein the focal path is a circular path.

15. The method as claimed in claim 5, wherein the focal path is a circular path.

16. An image reconstruction method for computed tomography, comprising:

obtaining output data corresponding to a scanned object;

filtering the output data; and backprojecting the filtered output data three-dimensionally to produce at least one slice of a layer of the object, the slice representing absorption values obtained from a voxel associated with the layer of the object, wherein the filtering is carried at least in a direction of a tangent to the focal path belonging to a respective focal position, and normalization is carried out for each voxel considered.

17. The method as claimed in claim 16, wherein before the filtering, the method includes converting the output data in the form of rays $P(\alpha,\beta,q)$ into parallel data present in parallel ray geometry in the form of rays $P(\theta,\beta,q)$ and $P(\theta,p,q)$, where $\alpha$ is a focus angle $\beta$ is a fan angle q is a line index of the detector system corresponding to the z coordinate, $\theta = \alpha + \beta$ is a parallel fan angle $p = R_F \sin(\beta)$ is a parallel coordinate corresponding to the distance of the ray from the axis of rotation (system axis), and $R_F$ is the radius of a focal path.

* * * * *